United States Patent [19]

Tyers

[11] Patent Number: 4,835,173

[45] Date of Patent: May 30, 1989

[54] METHOD OF MEDICAL TREATMENT

[75] Inventor: Michael B. Tyers, Ware, England

[73] Assignee: Glaxo Group Limited, London, England

[21] Appl. No.: 133,887

[22] Filed: Dec. 16, 1987

[30] Foreign Application Priority Data

Dec. 17, 1986 [GB] United Kingdom ............... 8630071

[51] Int. Cl.$^4$ .......................................... A61K 31/415
[52] U.S. Cl. ................................................... 514/397
[58] Field of Search ........................................ 514/397

[56] References Cited

U.S. PATENT DOCUMENTS

| | | | |
|---|---|---|---|
| 4,721,720 | 1/1988 | Wootton et al. | 514/872 |
| 4,753,789 | 6/1988 | Tyers et al. | 514/872 |

FOREIGN PATENT DOCUMENTS

| | | |
|---|---|---|
| 2153821A | 8/1985 | United Kingdom . |
| 2193633A | 2/1988 | United Kingdom . |

OTHER PUBLICATIONS

Article, New Glaxo Drug Relieves Worry, London Daily Telegraph, 18th Dec. 1986.

*Primary Examiner*—Stanley J. Friedman
*Attorney, Agent, or Firm*—Bacon & Thomas

[57] ABSTRACT

The invention relates to the use of 1,2,3,9-tetrahydro-9-methyl-3-[(2-methyl-1H-imidazol-1-yl)methyl]-4H-carbazol-4-one and physiologically acceptable salts and solvates thereof in the treatment of depression.

6 Claims, No Drawings

METHOD OF MEDICAL TREATMENT

This invention relates to a new medical use for a heterocyclic compound and pharmaceutical compositions containing it. In particular it relates to the use of 1,2,3,9-tetrahydro-9-methyl-3-[(2-methyl-1H-imidazol-1-yl)methyl]-4H-carbazol-4-one and the physiologically acceptable salts and solvates thereof in the treatment of depression.

The aforementioned compound may be represented by the formula (I):

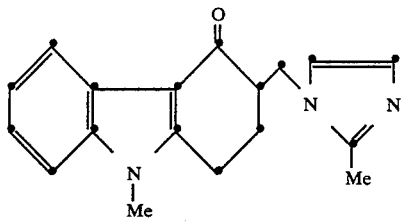

and is disclosed in UK Patent Specification No. 2153821A.

Suitable physiologically acceptable salts of the compound of formula (I) include acid addition salts formed with organic or inorganic acids for example, hydrochlorides, hydrobromides, sulphates, phosphates, citrates, fumarates and maleates. The solvates may, for example, be hydrates.

The aforementioned specification also discloses physiologically acceptable equivalents of the compound of formula (I), i.e. physiologically acceptable compounds which are converted in vivo into the parent compound of formula (I).

The compound of formula (I) is described in the aforementioned specification as a potent and selective antagonist of 5-hydroxytryptamine (5-HT) at 'neuronal' 5-HT receptors of the type located on terminals of primary afferent nerves. Receptors of this type are now designated as 5-HT$_3$ receptors and are also present in the central nervous system. 5-HT occurs widely in the neuronal pathways in the central nervous system and disturbance of these 5HT containing pathways is known to alter behavioural syndromes such as mood, psychomotor activity, appetite and memory.

The compound is described as being of use in the treatment of a human or animal subject suffering from a condition caused by a disturbance of neuronal 5-HT function, for example in the treatment of a human subject suffering from migraine pain or a psychotic disorder such as schizophrenia. It is also stated that the compound may be useful in the treatment of conditions such as anxiety, obesity and mania.

We have now found that the compound of formula (I) may be used in the treatment of depression.

Accordingly the invention provides a method of treatment of a subject, in particular a human subject, suffering from depression, which comprises administering to the subject an effective amount of the compound of formula (I) or a physiologically acceptable salt or solvate thereof.

References in this specification to treatment include prophylactic treatment as well as the acute alleviation of symptoms.

A preferred form of the compound of formula (I) is the hydrochloride, particularly in a hydrated form (e.g. the dihydrate).

In a further aspect, the invention provides a pharmaceutical composition which comprises an effective amount of the compound of formula (I) or a physiologically acceptable salt or solvate (e.g. hydrate) thereof, for use in medicine, particularly human medicine, for the treatment of depression.

In a yet further aspect, the invention provides for the use of the compound of formula (I) or a physiologically acceptable salt or solvate thereof, for the manufacture of a medicament for the treatment of depression.

Pharmaceutical compositions for use in accordance with the present invention may be formulated in conventional manner using one or more physiologically acceptable carriers or excipients.

Thus the compound of formula (I) and its physiologically acceptable salts and solvates may be formulated for oral, buccal, parenteral, rectal or transdermal administration or in a form suitable for administration by inhalation or insufflation (either through the mouth or the nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compound of formula (I) may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredients may be in powder form for constitution with a suitable vehicle, e.g. sterile pyrogen-free water, before use.

The compound of formula (I) may also be formulated in rectal compositions such as suppositories or retention enemas, e.g. containing conventional suppository bases such as cocoa butter or other glycerides.

In addition to the formulations described previously, the compound may also be formulated as depot preparation. Such long acting formulations may be administered by implantation (for example subcutaneously, transcutaneously or intramuscularly) or by intramuscular injection. Thus, for example, the compound of formula (I) may be formulated with suitable polymeric or hydrophobic materials (for example as an emulsion in an acceptable oil) or ion exchange resins, or as sparingly soluble derivatives, for example, as a sparingly soluble salt.

A proposed dose of the compound of the invention for administration to a human (of approximately 70 kg body weight) is 0.05 to 20 mg, preferably 0.1 to 10 mg of the active ingredient per unit dose, expressed as the weight of free base. The unit does may be administered, for example, 1 to 4 times per day. The dose will depend on the route of administration. It will be appreciated that it may be necessary to make routine variations to the dosage depending on the age and weight of the patient as well as the severity of the condition to be treated.

The compound of formula (I) may be prepared by the processes described in UK Patent Specification No. 2153821A and the following examples illustrate its preparation and salt formation. Temperatures are in °C.

EXAMPLE 1

1,2,3,9-Tetrahydro-9-methyl-3-[(2-methyl-1H-imidazol-1-yl)methyl]-4H-carbazol-4-one A solution of 3-[(dimethylamino)methyl]-1,2,3,9-tetrahydro-9-methyl-4H-carbazol-4-one hydrochloride (1.7 g) in water (17 ml) was treated with 2-methylimidazole (1.4 g) and then heated under reflux for 20 h. The cooled mixture was filtered and the residue washed with water ($3 \times 15$ ml) to give a product (1.7 g) m.p. 221°–221.5°. This material was recrystallised from methanol to give the title compound (1.4 g) m.p. 231°–232°.

EXAMPLE 2

1,2,3,9-Tetrahydro-9-methyl-3-[(2-methyl-1H-imidazol-1-yl)methyl]-4H-carbazol-4-one hydrochloride dihydrate 1,2,3,9-Tetrahydro-9-methyl-3-[(2-methyl-1H-imidazol-1-yl)methyl]-4H-carbazol-4-one (18.3 g) in a hot mixture of isopropanol (90 ml) and water (18.3 ml) was treated with concentrated hydrochloric acid (6.25 ml). The hot mixture was filtered and the filtrate diluted with isopropanol (90 ml) and stirred at room temperature for 17 h, cooled to 2° and the solid filtered off (21.6 g). A sample (6 g) was recrystallized from a mixture of water (6 ml) and isopropanol (10 ml) to give the title compound as a white crystalline solid (6 g) m.p. 178.5°–179.5°.

Analysis Found: C, 59.45; H, 6.45; N, 11.5. $C_{18}H_{19}N_3O \cdot HCl \cdot 2H_2O$ requires C, 59.1; H, 6.6; N, 11.5%.

Water assay Found: 10.23% $C_{18}H_{19}N_3O \cdot HCl \cdot 2H_2O$ requires 9.85%

The following examples illustrate pharmaceutical formulations for use according to the invention, containing 1,2,3,9-tetrahydro-9-methyl-3-[(2-methyl-1H-imidazol-1-yl)methyl]-4H-carbazol-4-one hydrochloride dihydrate as the active ingredient (1.25 g of the hydrochloride dihydrate contains 1.00 g of the free base).

TABLETS FOR ORAL ADMINISTRATION

Tablets may be prepared by the normal methods such as direct compression or wet granulation.

The tablets may be film coated with suitable film forming materials, such as hydroxypropyl methylcellulose, using standard techniques. Alternatively the tablets may be sugar coated.

| Direct Compression Tablet | mg/tablet |
| --- | --- |
| Active Ingredient | 4.688 |
| Calcium Hydrogen Phosphate BP* | 83.06 |
| Croscarmellose Sodium NF | 1.8 |
| Magnesium Stearate BP | 0.45 |
| Compression weight | 90.0 |

*of a grade suitable for direct compression.

The active ingredient is passed through a 60 mesh sieve, blended with the calcium hydrogen phosphate, croscarmellose sodium and magnesium stearate. The resultant mix is compressed into tablets using a Manesty F3 tablet machine fitted with 5.5 mm, flat bevelled edge punches.

| Sub-Lingual Tablet | mg/tablet |
| --- | --- |
| Active Ingredient | 2.5 |
| Compressible Sugar NF | 62.0 |
| Magnesium Stearate BP | 0.5 |
| Compression Weight | 65.0 |

The active ingredient is sieved through a suitable sieve, blended with the excipients and compressed using suitable punches. Tablets of other strengths may be prepared by altering either the ratio of active ingredient to excipients or the compression weight and using punches to suit.

| Wet Granulation Conventional Tablet | mg/tablet |
| --- | --- |
| Active Ingredient | 2.5 |
| Lactose BP | 151.0 |
| Starch BP | 30.0 |
| Pregelatinised Maize Starch BP | 15.0 |
| Magnesium Stearate BP | 1.5 |
| Compression Weight | 200.0 |

The active ingredient is sieved through a suitable sieve and blended with lactose, starch and pregelatinised maize starch. Suitable volumes of purified water are added and the powders are granulated. After drying, the granules are screened and blended with the magnesium stearate. The granules are then compressed into tablets using 7 mm diameter punches.

Tablets of other strengths may be prepared by altering the ratio of active ingredient to lactose or the compression weight and using punches to suit.

| Sub-Lingual Tablet | mg/tablet |
| --- | --- |
| Active Ingredient | 2.5 |
| Mannitol BP | 56.5 |
| Hydroxypropylmethylcellulose | 5.0 |

| Sub-Lingual Tablet | mg/tablet |
|---|---|
| Magnesium Stearate BP | 1.0 |
| Compression Weight | 65.0 |

The active ingredient is sieved through a suitable sieve and blended with the mannitol and hydroxypropylmethylcellulose. Suitable volumes of purified water are added and the powders are granulated. After drying, the granules are screened and blended into tablets using suitable punches.

Tablets of other strengths may be prepared by altering the ratio of active ingredient to mannitol or the compression weight and punches to suit.

| CAPSULES | mg/capsule |
|---|---|
| Active Ingredient | 2.5 |
| *Starch 1500 | 96.5 |
| Magnesium Stearate BP | 1.0 |
| Fill Weight | 100.0 |

*a form of directly compressible starch.

The active ingredient is sieved and blended with the excipients. The mix is filled into size No. 2 hard gelatin capsules using suitable machinery. Other doses may be prepared by altering the fill weight an if necessary changing the capsule size to suit.

SYRUP

This may be either a sucrose or sucrose free presentation.

| A. Sucrose Syrup | mg/5 ml dose |
|---|---|
| Active Ingredient | 2.5 |
| Sucrose BP | 2750.0 |
| Glycerine BP | 500.0 |
| Buffer | |
| Flavour | |
| Colour | as required |
| Preservative | |
| Purified Water BP to | 5.0 ml |

The active ingredient, buffer, flavour, colour and preservative are dissolved in some of the water and the glycerine is added. The remainder of the water is heated to dissolve the sucrose and is then cooled. The two solutions are combined, adjusted to volume and mixed. The syrup is clarified by filtration.

| B. Sucrose-Free | mg/5 ml dose |
|---|---|
| Active Ingredient | 2.5 |
| Hydroxypropylmethylcellulose USP (viscosity type 4000) | 22.5 |
| Buffer | |
| Flavour | |
| Colour | as required |
| Preservative | |
| Sweetener | |
| Purified Water BP to | 5.0 ml |

The hydroxypropylmethylcellulose is dispersed in hot water, cooled and then mixed with an aqueous solution containing the active ingredient and the other components of the formulation. The resultant solution is adjusted to volume and mixed. The syrup is clarified by filtration.

INJECTIONS

The injection may be administered by the intravenous or subcutaneous route.

| | μg/ml |
|---|---|
| (i) Active Ingredient | 800 |
| Dilute Hydrochloric Acid BP | to pH 3.5 |
| Sodium Chloride Injection BP | to 1 ml |

The active ingredient is dissolved in a suitable volume of Sodium Chloride Injection BP, the pH of the resultant solution is adjusted to pH 3.5 with dilute hydrochloric acid BP then the solution is made to volume with sodium chloride injection BP and thoroughly mixed. The solution is filled into Type 1 clear glass 5 ml ampoules which are sealed under a headspace of air, by fusion of the glass then sterilised by autoclaving at 120° for not less than 15 minutes.

| | mg/ml |
|---|---|
| (ii) Active ingredient | 0.80 |
| Citric Acid Monohydrate BP | 0.50 |
| Sodium Citrate BP | 0.25 |
| Sodium Chloride BP | 9.00 |
| Water for Injections USP to | 1.0 ml |

The citric acid monohydrate, active ingredient, sodium citrate and sodium chloride are dissolved in the major portion of the water for injections, the solution is made to volume and mixed thoroughly. After filtration, the solution is filled under air into ampoules which are sealed by fusion of the glass. The ampoules are sterilised by autoclaving for at least 15 minutes at 121°–124° C.

SUPPOSITORY

| Active Ingredient | 5.0 mg |
|---|---|
| *Witepsol H15 to | 1.0 g |

*Witepsol H15 is a proprietary grade of Adeps Solidus Ph. Eur.

A suspension of the active ingredient is prepared in the molten Witepsol and filled, using suitable machinery, into 1 g size suppository moulds.

I claim:

1. A method for the treatment of depression in a human or animal subject suffering from or susceptible to depression, which comprises administering to the human or animal subject an effective amount for treatment of depression in said subject of 1,2,3,9-tetrahydro-9-methyl-3-[(2-methyl-1H-imidazol-1-yl)methyl-]4H-carbazol-4-one or a physiologically acceptable salt or solvate thereof.

2. A method according to claim 1 wherein said 1,2,3,9-tetrahydro-9-methyl-3-[(2-methyl-1H-imidazol-1-yl)methyl]-4H-carbazol-4-one is administered in the form of a hydrochloride salt.

3. A method according to claim 1 wherein said 1,2,3,9-tetrahydro-9-methyl-3-[(2-methyl-1H-imidazol-1-yl)methyl]-4H-carbazol-4-one is administered in the form of the hydrochloride dihydrate salt.

4. A method according to claim 1 wherein said 1,2,3,9-tetrahydro-9-methyl-3-[(2-methyl-1H-imidazol-1-yl)methyl]-4H-carbazol-4-one or a physiologically acceptable salt or solvate thereof is administered in a dose of 0.05 to 20 mg from 1 to 4 times per day, the dose being expressed as the weight of free base.

5. A method according to claim 4 wherein said dose is from 0.1 to 10 mg from 1 to 4 times per day.

6. A method according to claim 1 wherein said 1,2,3,9-tetrahydro-9-methyl-3-[(2-methyl-1H-imidazol-1-yl)methyl]-4H-carbazol-4-one is administered orally, bucally, parenterally, rectally or as a depot preparation.

* * * * *